United States Patent [19]

Shander et al.

[11] Patent Number: 5,474,763

[45] Date of Patent: Dec. 12, 1995

[54] REDUCTION OF HAIR GROWTH

[76] Inventors: Douglas Shander, 16112 Howard Landing Dr., Gaithersburg, Md. 20878; Margaret G. Funkhouser, 1322 S. Pollard St., Arlington, Va. 22204

[21] Appl. No.: 212,012

[22] Filed: Mar. 11, 1994

[51] Int. Cl.$^6$ .............................. A61K 7/06; A61K 7/15; A61K 7/155

[52] U.S. Cl. ................................. 424/73; 424/62; 424/69; 424/70.1; 514/557; 514/844; 514/852; 514/880; 514/881

[58] Field of Search ................. 424/73, 70.1, 62, 424/69; 514/557, 844, 852, 880, 881

[56] References Cited

U.S. PATENT DOCUMENTS

| | | | |
|---|---|---|---|
| 3,426,137 | 2/1969 | Philpitt et al. | 424/330 |
| 4,039,669 | 8/1977 | Beyler et al. | 424/243 |
| 4,139,638 | 2/1979 | Neri et al. | 424/324 |
| 4,161,540 | 7/1979 | Neri et al. | 424/324 |
| 4,191,775 | 3/1980 | Glen | 424/304 |
| 4,269,831 | 5/1981 | Ferrari et al. | 424/241 |
| 4,344,941 | 8/1982 | Wiechert et al. | 424/243 |
| 4,370,315 | 1/1983 | Greff et al. | 424/94 |
| 4,439,432 | 3/1984 | Peat | 424/240 |
| 4,720,489 | 1/1988 | Shander | 514/171 |
| 4,885,289 | 12/1989 | Breuer et al. | 514/170 |
| 5,095,007 | 3/1992 | Ahluwalia | 514/23 |
| 5,096,911 | 3/1992 | Ahluwalia et al. | 514/380 |
| 5,132,293 | 7/1992 | Shander et al. | 514/46 |
| 5,143,925 | 9/1992 | Shander et al. | 514/378 |
| 5,271,942 | 12/1993 | Heverhagen | 424/451 |

FOREIGN PATENT DOCUMENTS

| | | |
|---|---|---|
| 0413528 | 2/1991 | European Pat. Off. |
| 0532219A2 | 3/1993 | European Pat. Off. |
| 1458349 | 12/1976 | United Kingdom . |
| 85/02543 | 6/1985 | WIPO . |
| 86/02269 | 4/1986 | WIPO . |
| 92/00069 | 1/1992 | WIPO . |
| 92/03140 | 3/1992 | WIPO . |
| 92/11007 | 7/1992 | WIPO . |

OTHER PUBLICATIONS

Messenger, The Journal of Investigative Dermatology, vol. 101, No. 1, Supplement, Jul. 1993, pp. 4S–9S.
Sato, Biology and Disease of the Hair, 1975, pp. 3–13.
Simpson et al. British Journal of Dermatology, (1979) 100, pp. 687–692.
Burdick et al., Br. J. Derm. (1970) 82, Supplement 6, pp. 19–25.
Goos et al., Arch. Dermatol. Res. (1982) 273:333–341.
Girard et al., Arch. Dermatol. Res. 269, 281–290 (1980).
Champion, The Medical Journal of Australia, vol. 149, No. 4, Aug. 15, 1988, pp. 203–213.
Seiler et al., Int. J. Biochem., vol. 21, No. 4, pp. 425–432, 1989 hairless mice 5FMOrn.
Janssen et al., Clinica Chimica Acta., 113 (1981) pp. 213–216.
Kaiser–Kupper et al., Opthalmology, Apr. 1981, vol., 88 No. 4, pp. 302–306.
Alonso et al., Biochem. J. (1989) 259, 131–138 Swiss mole albino mice fed diet gabaculine (I.P.) and diet deprived of argenine/alanin.
Smith et al., Cell Physiol., (1979) 98:475–482.
Bolkenius et al., Biochem. J. (1990) 268, pp. 409–414 DL–canaline I.P. mole mice.
Daune et al., Biochem J. (1988) 253, pp. 481–488 5 FMOrn I.P. mice.
Yuctel C.A. 115:189747f (1991) of E.P. 413528 (Feb. 20, 1991).
Salzer et al. C.A. 113:126168f (1990) of Hear. Res. 46 (1–2) 101–112 (1990) (DFMO–a–Difluoromethyl armithine) causes loss of hair cells).
C.A. 117:157401p of WO/PCT 92/11007 (Jul. 9, 1992).
C.A. 116:221336e of WO/PCT 92/03140 (Mar. 5, 1992).
C.A. 116:158565m of WO/PCT 92/00069 (Jan. 9, 1992).
C.A. 105: 158815r of WO/PCT 86/02269 (Apr. 24, 1986).
C.A. 103: 128804c of WO/PCT 85/02543 (Jun. 20, 1985).

*Primary Examiner*—Shep K. Rose
*Attorney, Agent, or Firm*—Fish & Richardson

[57] ABSTRACT

Mammalian hair growth is reduced by applying to the skin a composition including an inhibitor of ornithine aminotransferase.

11 Claims, No Drawings

REDUCTION OF HAIR GROWTH

The invention relates to a method of reducing unwanted hair growth in mammals.

A main function of mammalian hair is to provide environmental protection. However, that function has largely been lost in humans, in whom hair is kept or removed from various parts of the body essentially for cosmetic reasons. For example, it is generally preferred to have hair on the scalp but not on the face.

Various procedures have been employed to remove unwanted hair, including shaving, electrolysis, depilatory creams or lotions, waxing, plucking, and therapeutic antiandrogens. These conventional procedures generally have drawbacks associated with them. Shaving, for instance, can cause nicks and cuts as well as ingrown hairs resulting in inflammatory lesions, and can also promote the perception of an increase in the rate of hair regrowth. Shaving also can leave stubble. Electrolysis, on the other hand, can keep a treated area free of hair for prolonged periods of time, but can be expensive, painful, and sometimes leaves scarring. Depilatory creams, though very effective, typically are not recommended for frequent use due to their high irritancy potential. Waxing and plucking can cause pain, discomfort, and poor removal of short hair. Finally, antiandrogens—which have been used to treat female hirsutismp13 can have unwanted side effects.

It has previously been disclosed that the rate and character of hair growth can be altered by applying to the skin inhibitors of certain enzymes. These inhibitors include inhibitors of 5-alpha reductase, ornithine decarboxylase, S-adenosylmethionine decarboxylase, gammaglutamyl transpeptidase, and transglutaminase. See, for example, Breuer et al., U.S. Pat. No. 4,885,289; Shander, U.S. Pat. No. 4,720,489; Ahluwalia, U.S. Pat. No. 5,095,007; Ahluwalia et al., U.S. Pat. No. 5,096,911; Shander et al., U.S. Pat. No. 5,132,293; and Shander et al., U.S. Pat. No. 5,143,925.

The enzyme ornithine aminotransferase catalyzes the reversible conversion of ornithine and alpha ketoglutarate to delta-1-pyrroline-5-carboxylate and glutamate. Pyrroline-5-carboxylate is an intermediate precursor of proline.

It has now been found that unwanted mammalian (including human) hair growth—particularly androgen-stimulated hair growth—can be inhibited by applying to the skin a composition including an ornithine aminotransferase (OAT) inhibitor in an amount effective to reduce hair growth. The unwanted hair growth which is reduced may be normal hair growth, or hair growth that results from an abnormal or diseased condition.

Among the inhibitors of OAT that can be used are irreversible inhibitors of OAT such as 5-fluoromethylornithine (6-fluoro-2,5-diaminohexanoic acid, 5-FMOrn), (S)-2-amino-4-amino-oxybutyric acid (Canaline), and 3-amino-2,3-dihydrobenzoic acid (Gabaculin). Reversible inhibitors (competitive and non-competitive) can also be used.

The inhibitor of OAT preferably is incorporated in a topical composition which includes a non-toxic dermatologically acceptable vehicle or carrier which is adapted to be spread upon the skin. Examples of suitable vehicles are acetone, alcohols, or a cream, lotion, or gel which can effectively deliver the active compound. One such vehicle is disclosed in co-pending application PCT/U.S. 93/0506A. In addition, a penetration enhancer may be added to the vehicle to further enhance the effectiveness of the formulation.

The concentration of the inhibitor in the composition may be varied over a wide range up to a saturated solution, preferably from 0.1% to 30% by weight or even more; the reduction of hair growth increases as the amount of inhibitor applied increases per unit area of skin. The maximum amount effectively applied is limited only by the rate at which the inhibitor penetrates the skin. Generally, the effective amounts range from 100 to 3000 micrograms or more per square centimeter of skin.

The composition should be topically applied to a selected area of the body from which it is desired to reduce hair growth. For example, the composition can be applied to the face, particularly to the beard area of the face, i.e., the cheek, neck, upper lip, and chin. The composition can also be applied to the legs, arms, torso or armpits. The composition is particularly suitable for reducing the growth of unwanted hair in women suffering from hirsutism or other conditions. In humans, the composition should be applied once or twice a day, or even more frequently, for at least three months to achieve a perceived reduction in hair growth. Reduction in hair growth is demonstrated when the frequency of hair removal (shaving, tweezing, depilatory use, waxing) is reduced, or the subject perceives less hair on the treated site, or quantitatively, when the weight of hair removed by shaving (i.e., hair mass) is reduced. Benefits of reduced hair removal frequency include convenience and less skin irritation.

Male intact Golden Syrian hamsters are considered acceptable models for human beard hair growth in that they display oval shaped flank organs, one on each side, each about 8 mm. in major diameter, which grow thick black and coarse hair similar to human beard hair. These organs produce hair in response to androgens in the hamster. To evaluate the effectiveness of a particular OAT inhibitor, the flank organs of each of a group of hamsters are depilated by applying a thioglycolate based chemical depilatory (Surgex). To one organ of each animal 10–25 µl. of vehicle alone once a day is applied, while to the other organ of each animal an equal amount of vehicle containing an OAT inhibitor is applied. After thirteen applications (one application per day for five days a week), the flank organs are shaved and the amount of recovered hair (hair mass) from each is weighed. Percent-reduction of hair growth is calculated by subtracting the hair mass (mg) value of the test compound treated side from the hair mass value of the vehicle treated side; the delta value obtained is then divided by the hair mass value of the vehicle treated side, and the resultant number is multiplied by 100.

The above-described assay will be referred to herein as the "Golden Syrian hamster" assay. Preferred compositions provide an reduction in hair growth of at least about 35%, more preferably at least about 50%, and most preferably at least about 70% when tested in the Golden Syrian hamster assay.

A number of OAT inhibitors were tested in the Golden Syrian hamster assay; the results are presented in Table 1. The vehicle used in the compositions tested was 68% deionized water, 16% absolute ethanol, 5% propylene glycol, 5% dipropylene glycol, 4% benzoyl alcohol, and 2% propylene carbonate.

TABLE I

| Treatments | (n) | (mean ± SEM) Treated | Untreated | % Reduction |
|---|---|---|---|---|
| 5% 5-FMOrn | 8 | .616 ± .15 | 1.657 ± .15 | 66.02 ± 6.30 |
| 15% 5-FMOrn | 8 | .322 ± .07 | 2.065 ± .17 | 84.55 ± 2.47 |
| 10% Gabaculin | 8 | 1.365 ± .14 | 2.381 ± .21 | 43.06 ± 2.72 |
| 25% Gabaculin | 8 | 1.266 ± .11 | 2.556 ± .31 | 48.08 ± 5.00 |

TABLE I-continued

| Treatments | (n) | (mean ± SEM) Treated | Untreated | % Reduction |
|---|---|---|---|---|
| 2% Canaline |  | 1.553 ± .20 | 1.996 ± .25 | 20.99 ± 7.70 |
| 10% Canaline |  | .790 ± .11 | 1.466 ± .20 | 44.50 ± 7.40 |
| Control |  | 2.294 ± .18 | 2.465 ± .25 | 2.65 ± 8.52 |

The following assay for OAT activity based on the procedure of O'Donnell et al., *Analytical Biochemistry* 90, 41–46 (1978) was adapted for OAT measurements in hair follicles, and can be used to evaluate the effectiveness of OAT inhibitors in reducing OAT activity.

The product of OAT activity, pyrroline-5-carboxylic acid (P5C), was measured by reverse-phase HPLC analysis of dihydroquinazolium ion (DHQ). DHQ is a reaction product of PSC and o-aminobenzylaldehyde (OAB). The analysis was performed with a Waters 490 UV detector. The amount of DHQ formed was directly proportional to the concentration of P5C. The sensitivity of the Waters 490 UV detector had been determined to be above 100 picomoles of PSC injected and was reasonably linear.

Initial assays of flank organ follicle OAT activity were conducted employing saturating doses of ornithine (350 mM). The OAT mediated conversion of ornithine to P5C was monitored by measuring in vitro PSC formation, resulting in time and concentration dependent increases in PSC.

Assays (including the initial assays) were conducted utilizing excised hamster flank organ follicles. The excised hamster follicles were diluted in assay buffer (2 follicles/300 μl) and then were minced with scissors and homogenized with a sonicator. The resultant homogenate was centrifuged to obtain a cytosolic supernatant which was assayed for OAT. Samples were incubated for one hour with either Gabaculin, L-Canaline, or 5-FMOrn at 1 mM, 100 μM, 10 μM, and 1 μM concentrations. The concentration of P5C was then assayed. The results are provided in Table II. Gabaculin the most potent inhibitor and completely inhibited OAT at a concentration of 100 μM; 75% inhibition was observed at a concentration of 10 μM, and no inhibition was seen at a concentration of 1 μM. L-Canaline inhibited OAT completely at a concentration of 1 mM, 25% inhibition was seen at a concentration of 100 μM, and no inhibition was shown at a concentration of 10 and 1 μM concentrations. 5-FMOrn demonstrated 83% OAT inhibition at a concentration of 1 mM. No OAT inhibition was exhibited by 5-FMOrn at concentrations of 100 μM, 10 μM and 1 μM.

TABLE II

| Compound | Final Concentration | | Percent Inhibition | nm P5C formed/fol/1 hr |
|---|---|---|---|---|
| Gabaculin | 1 mM | pH = 4.5 | 100 | n.d. |
|  | 100 μM | (pH = 7.5) | 100 | n.d. |
|  | 10 μM |  | 74.268 | 5.057 |
| L-Canaline | 1 μM |  | 0.089 | 19.637 |
|  | 1 mM | pH = 7.5 | 100 | n.d. |
|  | 100 μM |  | 25.653 | 14.612 |
|  | 10 μM |  | none | 24.096 |
|  | 1 μM |  | none | 29.859 |
| 5-FMOrn | 1 mM | pH = 7.5 | 83.036 | 3.334 |
|  | 100 μM |  | 0.471 | 19.562 |
|  | 10 μM |  | none | 29.327 |
|  | 1 μM |  | none | 31.419 |
| Control |  |  | 0.000 | 19.654 | n.d. = not detectable

It will be appreciated by those skilled in the art that the invention can be performed within a wide range of equivalent parameters of composition and conditions without departing from the spirit or scope of the invention or of any embodiment thereof.

We claim:

1. A method of reducing mammalian hair growth which comprises selecting an area of skin of a mammal from which hair is growing and from which reduced hair growth is desired; and applying to said area of skin of a mammal from which hair is growing and from which reduced hair growth is desired an inhibitor of ornithine aminotransferase in an amount effective to reduce hair growth.

2. The process of claim 1, wherein said inhibitor is 6-fluoro-2,5-diaminohexanoic acid.

3. The process of claim 1, wherein said inhibitor is (S)-2-amino-4-amino-oxybutyric acid.

4. The process of claim 1, wherein said inhibitor is 3-amino-2,3-dihydrobenzoic acid.

5. The process of claim 1, wherein said inhibitor is an irreversible inhibitor.

6. The process of claim 1, wherein the concentration of said inhibitor in said composition is between 1% and 30%.

7. The process of claim 1, wherein the composition is applied to the skin in an amount of from 100 to 3000 micrograms of said inhibitor per square centimeter of skin.

8. The process of claim 1, wherein the composition is applied to the skin on the face of said mammal.

9. The process of claim 1, wherein the composition provides a reduction in hair growth of at least 30% when tested in the Golden Syrian hamster assay.

10. The process of claim 1, wherein the composition provides a reduction in hair growth of at least 50% when tested in the Golden Syrian hamster assay.

11. The process of claim 1, wherein the composition provides a reduction in hair growth of at least 70% when tested in the Golden Syrian hamster assay.

* * * * *

UNITED STATES PATENT AND TRADEMARK OFFICE
CERTIFICATE OF CORRECTION

PATENT NO.  : 5,474,763

DATED       : December 12, 1995

INVENTOR(S) : Douglas Shander et al.

It is certified that error appears in the above-identified patent and that said Letters Patent is hereby corrected as shown below:

Col. 1, line 26, "hirsutismp13 can" should be
--hirsutism -- can--.

Col. 3, lines 18, 22, 27, and 28, "PSC" should be
--P5C--.

Signed and Sealed this

Twentieth Day of August, 1996

Attest:

BRUCE LEHMAN

Attesting Officer    Commissioner of Patents and Trademarks